United States Patent
Wolf

(10) Patent No.: US 8,729,049 B2
(45) Date of Patent: May 20, 2014

(54) LEAVEN-BASED MIXTURE

(75) Inventor: Gabrielle Wolf, Isernhagen (DE)

(73) Assignee: woresan GmbH, Isernhagen (DE)

( * ) Notice: Subject to any disclaimer, the term of this patent is extended or adjusted under 35 U.S.C. 154(b) by 0 days.

(21) Appl. No.: 13/498,498

(22) PCT Filed: Sep. 28, 2010

(86) PCT No.: PCT/EP2010/064333
§ 371 (c)(1),
(2), (4) Date: Mar. 27, 2012

(87) PCT Pub. No.: WO2011/036304
PCT Pub. Date: Mar. 31, 2011

(65) Prior Publication Data
US 2012/0184507 A1    Jul. 19, 2012

(30) Foreign Application Priority Data
Sep. 28, 2009  (EP) ................. 09171506

(51) Int. Cl.
A61K 31/716    (2006.01)
A21D 8/04      (2006.01)
A61K 35/74     (2006.01)
A61K 36/899    (2006.01)

(52) U.S. Cl.
CPC ........... A21D 8/045 (2013.01); A61K 35/74 (2013.01); A61K 36/899 (2013.01)
USPC ................................ 514/54; 435/101

(58) Field of Classification Search
CPC ................ A21D 8/045; A61K 35/74
USPC ............................. 514/54; 435/101
See application file for complete search history.

(56) References Cited

U.S. PATENT DOCUMENTS
2005/0063964 A1    3/2005 Wolf

FOREIGN PATENT DOCUMENTS

| | | |
|---|---|---|
| CH | 623207 A5 | 5/1981 |
| DE | 3802840 A1 | 8/1989 |
| EP | 0530861 A2 | 3/1993 |
| EP | 1321122 A1 | 6/2003 |
| EP | 1458334 B1 | 3/2006 |
| WO | 00/10395 | 3/2000 |
| WO | 03/075868 A1 | 9/2003 |

OTHER PUBLICATIONS

Katina et al. Fermentation-induced changes in the nutritional value of native or germinated rye. J Cereal Sci 46:348-355, 2007.*
Wilhelmson et al. Development of a Germination Process for Producing High β-Glucan, Whole Grain Food Ingredients from Oat. Cereal Chem 78:715-720, 2001.*

* cited by examiner

*Primary Examiner* — Brandon Fetterolf
*Assistant Examiner* — Yih-Horng Shiao
(74) *Attorney, Agent, or Firm* — Dardi & Herbert, PLLC; Curtis B. Herbert

(57) ABSTRACT

An embodiment is a mixture obtainable by a process comprising the following steps: a) adding a culture comprising sprouted rye grains and water to a rye fine or coarse meal and subjecting the mixture to a process of heating to 30-34° C. within 3 to 5 hours, a strong maltose formation being initiated from enzymatic reactions; b) followed by a further addition of rye fine or coarse meal, water and a bacteriological inoculum from the group of heterofermentative lactic-acid bacteria; c) acidifying the mixture until the metabolic activity of the microorganisms ceases, and optionally pasteurizing at 90-95° C.; d) separating the mixture by centrifugation into a solution and a precipitate, after which the solution is optionally filtered at least once.

10 Claims, No Drawings

LEAVEN-BASED MIXTURE

CROSS REFERENCE TO RELATED APPLICATIONS

This application is a national stage filing of PCT application number PCT/EP2010/064333 filed on Sep. 28, 2010, which claims priority to European patent application number 09171506,0 filed on Sep. 28, 2009, both of which are hereby incorporated herein by reference.

TECHNICAL FIELD

The present invention relates to a leaven-based mixture, a medicament containing the mixture according to the invention, the use of the mixture according to the invention for treating diseases, and a process for preparing the mixture.

INTRODUCTION TO THE INVENTION

From DE-A-38 02 840 2, a method for the preparation of a fermentation product containing lactic acid and viable lactic-acid bacteria by acidifying an aqueous slurry of a baked leaven-based bread mass in a lactic acid containing medium has already been known, the baked product of an acidified bread dough being employed as the bread mass. This fermentation product is said to be employable, inter alia, as an auxiliary agent in the treatment of the holistic organism of humans, animals and plants.

From DE-A-38 46 186, it has also been known already to employ preparations obtained from the fermentation sludge of spontaneous acidification of leaven breads, for example, as a pack aggregate material for the treatment of chronic inflammatory diseases of the skin.

From DT-B-26 11 972, it has already been known to acidify the leaven bacteria in the cereal mash forming the pre-dough until any bacteriological metabolic activity ceases for the preparation of a leaven for the preparation of breads and bakery products from cereal coarse and/or fine meals.

In EP-B-0 530 861, a topical antimicrobial pharmaceutical composition which comprises a mixture of $C_6$ to $C_{18}$ fatty acids has been disclosed.

DE-U-299 23 627 relates to a curative and care agent for promoting the blood flow, for releasing muscular tension, for skin cleaning and for skin regeneration, which is applied to body parts or used as an additive to a water bath. The product is characterized by being formed from a fermentation product of an acidified leaven. This document does not mention anything about a pretreatment of the rye coarse meal used as a substrate.

WO-A-00/10395 discloses a method for the preparation of a live liquid leaven product which has a plaque-forming capacity of at least $5 \times 10^8$ cfu/g of meal (dry matter) after cold storage for 10 weeks. No indications are given as to the fact that this product is suitable as a curative and care agent. In this document, calcium carbonate is employed as a buffer agent in order that the pH value of the mixture described therein does not decrease too much.

EP-A-1 458 334 relates to fermentation products of rye coarse or fine meals with heterofermentative lactic-acid bacteria, which have been treated with α-amylase prior to fermentation, a process for producing them, and application thereof as curatives and care agents.

SUMMARY OF THE INVENTION AND DETAILED DESCRIPTION

Surprisingly, it has been found that a novel mixture obtainable by a process comprising the following steps a) adding a culture comprising sprouted rye grains and water to a rye fine or coarse meal and subjecting the mixture to a process of heating to 30-34° C. within 3 to 5 hours, a strong maltose formation being initiated from enzymatic reactions;
b) followed by a further addition of rye fine or coarse meal, water and a bacteriological inoculum from the group of heterofermentative lactic-acid bacteria;
c) acidifying the mixture until the metabolic activity of the microorganisms ceases, and heating it to 90-95° C. until a metabolic activity can no longer be detected;
d) separating the mixture by centrifugation into a solution and a precipitate, after which the solution is optionally filtered at least once;

is suitable for use as a medicament.

The mixture according to the invention is characterized by a higher content of tocopherols and other active substances, such as α-tocotrienol, vitamin B1, B2, B6, folic acid as well as pantothenic acid, as compared to the fermentation products from EP-A-1 458 334.

The mixture according to the invention can be prepared by the process claimed according to the invention in which a sprouted cereal is subjected to processing with filtration and ultracentrifugation steps as described in further detail in the following. The process according to the invention comprises the following steps:

a) adding a culture comprising sprouted rye grains and water to a rye fine or coarse meal and subjecting the mixture to a process of heating to 30-34° C. within 3 to 5 hours, a strong maltose formation being initiated from enzymatic reactions;
b) followed by a further addition of rye fine or coarse meal, water and a bacteriological inoculum from the group of heterofermentative lactic-acid bacteria;
c) acidifying the mixture until the metabolic activity of the microorganisms ceases, and optionally pasteurizing at 90-95° C.;
d) separating the mixture by centrifugation into a solution and a precipitate, after which the solution is optionally filtered at least once.

In a particular embodiment of the process according to the invention, *Lactobacillus* DSM 6037 and/or *Lactobacillus* DSM 6129 are preferably employed.

According to the invention, the addition of a preservative can be dispensed with.

The fermentation product may typically be deep-frozen for breaking up the gel structure. After thawing, the brans present in the product are separated off, especially by means of an ultracentrifuge. This is optionally followed by another freezing. After the subsequent thawing, the product may optionally be purified by filtration in several steps to remove any turbid matter. This may be followed by a sterile filtration or sterilization with heating.

The mixture according to the invention may advantageously be employed as a medicinal product, for example, as a medicament, especially in a galenic formulation for external and/or internal administration.

For the applications, there may be used, in particular, lotions, ointments, sprays, creams, gels, tinctures, soaked compresses, patches, surgical drape, bandages, dressing materials, tampons, ampoules, sera, capsules.

The mixture according to the invention can be formulated, in particular, for a medicinal product or medicament that can be employed for the treatment of bacterial and/or viral infections and/or fungal infections.

For example, the mixture according to the invention is effective against onychomycoses, especially tinea unguium, which is caused by infection with *Trichophyton rubrum* and *Trichophyton mentagrophytes*, as well as tinea pedis. The mixture according to the invention may also be employed as a medicament for the treatment of acne-causing bacteria, such as *Propionibacterium acnes* or *Staphylococcus epidermidis*. The mixture has also proven useful for the treatment of infections with *Malassezia furfur*, which causes atopic/seborrhoic eczemas and other skin diseases. There may also be mentioned the treatment of infections with *Candida albicans*, which causes candidosis, an infectious disease of the mucosae, and occurs in the mouth, throat, esophagus, stomach, small and large intestines, and may also infest internal organs as an opportunistic pathogen in immunodeficiency diseases. For example, pneumonias may result in the presence of diseases such as cancer, sepsis or AIDS. The medicament according to the invention may also be employed for the prevention of fungal infections during the administration of antibiotics or cortisone-containing preparations by fungi infesting the skin and mucosae.

The mixture according to the invention also contains β-1,3-glucan. This product, which is otherwise obtained only in a hardly soluble form, is here dissolved in water and thus can be employed particularly well for processing in the medical field.

Since aqueous formulations can be employed without emulsifiers, which may cause allergies, this kind of processing is advantageous especially in medicinal products.

The mixture according to the invention may be employed, in particular, as a wound spray against abrasions and burns and for alleviating symptoms of varicella or other diseases affecting the skin, such as sunburn, but also for open blisters.

Another application is effected, for example, by means of a stick from which the medicinal product according to the invention is released for the treatment of tinea pedis or mycosis pedis. When treated with the mixture according to the invention, a fast alleviation of the itching and a reduction of the onychomycoses is found already after a few applications. This supports the healing effect of the medicament according to the invention. The medicament according to the invention may also be employed in the ear, nose and throat region, in particular, for treating infested mucosae. There may be mentioned, for example, dry mouth syndrome as well as fungal infestation in the mouth, nose and ear. Eczemas can also be alleviated in appearance and healed by topical application of the agent according to the invention.

The mixture according to the invention may be employed for eczema protection, skin protection against sunburn, further suppression of acne symptoms, reinfection by onychomycoses, infections that may occur during or after surgery, prevention of vaginal fungi and the like.

The medicinal product according to the invention may also be employed for infection prophylaxis.

EXAMPLES

To prepare the rye gel according to the invention, one part of rye meal 1150 is mixed with two parts of water, and a culture with 10% sprouted rye grains, based on the starting product, is added. To this mixture, fermentation media with *Lactobacillus* DSM 6037 and *Lactobacillus* DSM 6129 are added. This mixture is fermented for 24 to 48 hours at temperatures of from 30 to 34° C. After the start of the enzymatic reaction, the starting fermentation is initiated by mixing one part of rye meal 1150 with two parts of water. The fermentation is complete when a constant pH value establishes. The mixture obtained from the starting fermentation is admixed with 60 parts of water, based on the total volume of the starting fermentation. The fermentation time is another 24 to 48 hours at a typical temperature of from 30 to 34° C. until a constant pH value has been reached. This is followed by a thermal treatment for 3 to 5 hours at a temperature of from 92 to 95° C. No preservatives are added. A long shelf life is ensured by hot filling into sterile containers. The production step is followed by the separation processes to prepare the mixture.

The fermentation product is deep-frozen for breaking up the gel structure. After thawing, the brans present in the product are separated off by an ultracentrifuge. This is followed by another freezing. After rethawing, the product is purified from turbid matter in several steps in folded filters and cartridge filters, followed by sterile filtration with heating at 60° C.

Selected Parameters

| Test parameters | according to the invention | according to EP-A-1 458 334 |
|---|---|---|
| Content of tocopherol | 30 μg/100 ml | 1.4 μg/100 ml |
| α-tocopherol | 27 μg/100 ml | 1.4 μg/100 ml |
| β-tocopherol | <10 μg/100 ml | <1 μg/100 ml |
| γ-tocopherol | 10 μg/100 ml | <1 μg/100 ml |
| δ-tocopherol | <10 μg/100 ml | <1 μg/100 ml |
| α-tocotrienol | <10 μg/100 ml | <1 μg/100 ml |
| Content of vitamin $B_1$ | 9.2 μg/100 ml | result follows |
| Content of vitamin $B_2$ | 7.9 μg/100 ml | 1.9 μg/100 ml |
| Content of vitamin $B_6$ | 21.0 μg/100 ml | 24 μg/100 ml |
| Content of folic acid | 2.6 μg/100 ml | 0.2 μg/100 ml |
| Content of pantothenic acid | 330 μg/100 ml | 83 μg/100 ml |
| Content of nicotinic acid amide | 73 μg/100 ml | 72 μg/100 ml |

The content of β-1,3-glucan was 103 mg/l and is thus significantly lower than in comparable products according to the prior art. The corresponding value for the product obtained according to EP-A-1 458 334 is around 461 mg/l. The content of β-1,3-glucan was measured according to the MEBAK II 2.5.2 method by the Forschungszentrum Weihenstephan für Brau- and Lebensmittelqualität, Freising, Germany. MEBAK is an acronym for Mitteleuropäische Brautechnische Analyse-kommission e.V.

The invention claimed is:

1. A leaven-based mixture obtainable by a process comprising:
    a) adding a culture comprising sprouted rye grains and water to a rye fine or coarse meal to form a rye mixture and subjecting the rye mixture to a process of heating to 30-34° C. within 3 to 5 hours, with a strong maltose formation being initiated from enzymatic reactions;
    b) followed by a further addition to the rye mixture of rye fine or coarse meal, water and a bacteriological inoculum from a group of heterofermentative lactic-acid bacteria;
    c) acidifying the rye mixture until metabolic activity of the bacteria in the rye mixture ceases; and
    d) separating the rye mixture by centrifugation into a solution and a precipitate, wherein the leaven-based mixture comprises α-, β-, γ-, δ-tocopherol, α-tocotrienol, vitamins $B_1$, $B_2$, $B_6$, folic acid, pantothenic acid, nicotinic acid amide, and β-1,3-glucan, and wherein the content of tocopherol is 30 μg/100 ml or higher.

2. A medicament comprising the leaven-based mixture of claim 1.

3. The medicament of claim 2 in a galenic formulation for external and/or internal administration.

4. The medicament of claim 2 in a form chosen from the group consisting of lotions, ointments, sprays, creams, gels, tinctures, soaked compresses, patches, surgical drape, bandages, dressing materials, tampons, ampoules, sera, and capsules.

5. A method of using the leaven-based mixture of claim 1 comprising administering the leaven-based mixture to a patient for a treatment of an infection chosen from the group consisting of bacterial infections, viral infections, and fungal infections.

6. A method of using the leaven-based mixture of claim 1 comprising administering the leaven-based mixture to a patient for a treatment of a skin or mucosa illness chosen from the group consisting of skin injuries, burns of skin, burns of mucosa, acne, blisters, and eczema.

7. A process for preparing a leaven-based mixture comprising:
 a) adding a culture comprising sprouted rye grains and water to a rye fine or coarse meal to form a rye mixture and subjecting the rye mixture to a process of heating to 30-34° C. within 3 to 5 hours, with a strong maltose formation being initiated from enzymatic reactions;
 b) followed by a further addition to the rye mixture of rye fine or coarse meal, water and a bacteriological inoculum from a group of heterofermentative lactic-acid bacteria;
 c) acidifying the rye mixture until metabolic activity of the bacteria in the rye mixture ceases; and
 d) separating the rye mixture by centrifugation into a solution and a precipitate, wherein the leaven-based mixture comprises $\alpha$-, $\beta$-, $\gamma$-, $\delta$-tocopherol, $\alpha$-tocotrienol, vitamins $B_1$, $B_2$, $B_6$, folic acid, pantothenic acid, nicotinic acid amide, and $\beta$-1,3-glucan, and wherein the content of tocopherol is 30 µg/100 ml or higher.

8. The process according to claim 7, wherein said heterofermentative lactic-acid bacteria comprise *Lactobacillus* DSM 6037 and/or *Lactobacillus* DSM 6129.

9. The process according to claim 7 further comprising pasteurizing the mixture at 90-95° C. after the acidification of the rye mixture in step c) and before the separation of the rye mixture into the solution and the precipitate in step d).

10. The process according to claim 7 further comprising filtering the solution.

\* \* \* \* \*